(12) United States Patent
Svanerudh et al.

(10) Patent No.: US 6,565,514 B2
(45) Date of Patent: May 20, 2003

(54) METHOD AND SYSTEM FOR DETERMINING PHYSIOLOGICAL VARIABLES

(75) Inventors: Johan Svanerudh, Uppsala (SE); Sauli Tulkki, Uppsala (SE)

(73) Assignee: Radi Medical Systems AB, Uppsala (SE)

(*) Notice: Subject to any disclaimer, the term of this patent is extended or adjusted under 35 U.S.C. 154(b) by 0 days.

(21) Appl. No.: 09/938,312

(22) Filed: Aug. 24, 2001

(65) Prior Publication Data

US 2002/0072880 A1 Jun. 13, 2002

Related U.S. Application Data (60) Provisional application No. 60/227,594, filed on Aug. 25, 2000.

(51) Int. Cl.$^7$ ................................................ A61B 5/02
(52) U.S. Cl. ........................ 600/486; 600/485; 600/561
(58) Field of Search ............................... 600/485, 486, 600/561

(56) References Cited

U.S. PATENT DOCUMENTS

| | | | | |
|---|---|---|---|---|
| 5,662,107 A | * | 9/1997 | Sakariassen | 600/369 |
| 6,193,669 B1 | * | 2/2001 | Degany et al. | 600/486 |
| 6,296,615 B1 | * | 10/2001 | Brockway et al. | 600/486 |
| 6,343,514 B1 | * | 2/2002 | Smith | 73/719 |
| 6,409,677 B1 | * | 6/2002 | Tulkki | 60/561 |

OTHER PUBLICATIONS

Pijls et al. "Coronary Pressure Measurement and Fractional Flow Reserve" Heart. 1998; 80:539–542.*

Bech et al. "Usefulness of Fractional Flow Reserve to Predict Clinical Outcome After Balloon Angioplasty" Circulation. 1999;99:883–888.*

Pijls, et al. "Fractional Flow Reserve" Circulation. 1995;92:3183–3193.*

De Bruyne et al. "Relation Between Myocardial Fractional Flow Reserve Calculated from Coronary Pressure Measurements and Excercise–Induced Myocardial Ischemia" Circulation. 1995;92:39–46.*

Pijls, N.H.J., et al., "Measurement of Fractional Flow Reserve to Assess the Functional Severity of Coronary–Artery Stenoses", *The New England Journal of Medicine*, 334 (26): 1703–1708 (Jun. 27, 1996).

Wilson, R. "Assessing the Severity of Coronary–Artery Stenoses", *The New England Journal of Medicine*, 334 (26): 1735–1737 (Jun. 27, 1996).

Svanerudh, J. "Simple and effective new technique for diagnostics of stenosis", (2 pages), [online], Retrieved on May 7, 2002 from the Internet: <URL: http://www.svls.se/sektioner/mtf/arkiv.htm>.

* cited by examiner

*Primary Examiner*—Robert L. Nasser
*Assistant Examiner*—Patricia Mallari
(74) *Attorney, Agent, or Firm*—Foley & Lardner

(57) ABSTRACT

This invention relates to a method and system for monitoring, determining by measurement and calculation and graphically displaying physiological variables related to blood pressure. At least two physiological variables, arterial pressure (Pa) and distal coronary pressure ($P_d$), are detected by and derived from a guidewire-mounted pressure sensor. The Myocordial Fractional Flow Reserve ($FFR_{myo}$) is determined by calculating a ratio $P_d/P_a$ from the measured physiological variables ($P_a$, $P_d$) and a graph is formed and displayed of the data resulting from the calculation. The invention also provides an interactive graphical user interface system for controlling the calculation of and for displaying, in at least one screen on a display in a monitoring unit, intermediate and final results of the method.

29 Claims, 5 Drawing Sheets

METHOD AND SYSTEM FOR DETERMINING PHYSIOLOGICAL VARIABLES

This application is a Utility application based on and claiming priority to, Provisional application No. 60/227,594, filed Aug. 25, 2000.

The present invention relates to monitoring of physiological variables, and in particular it relates to a method, a system and an arrangement for monitoring, determining by measurement and calculation and graphically displaying physiological variables related to blood pressure. A user interface system, including a monitor having an interactive graphical display for presentation of said physiological parameters and selectable functions, is provided.

BACKGROUND OF THE INVENTION

For the purpose of monitoring physiological variables, such as arterial blood pressure, there are monitoring systems available comprising graphical displays, on which variations of the parameter of interest over time can be displayed and analyzed.

For determining the so called Myocordial Fractional Flow Reserve, $FFR_{myo}$, two pressures must be measured, namely the arterial pressure before a stenosis, and the pressure distally of the stensosis.

$FFR_{myo}$ is defined as maximum myocordial flow in the presence of a stenosis in the supplying epicardial coronary artery, divided by normal maximum flow. $FFR_{myo}$ is calculated by means of the formula:

$$FFR_{myo}=(P_d-P_v)/(P_a-P_v)=P_d/P_a, \text{ wherein}$$

$P_d$=arterial pressure at maximum hyperemia;
$P_a$=distal coronary pressure at maximum hyperemia;
$P_v$=central venous pressure at maximum hyperemia.

It is a lesion-specific index of the functional severity of the stenosis and can be obtained by intracoronary pressure measurement by the guidewire-mounted pressure sensor. During PTCA, balloon angioplastic or Percutaneaus Transluminal Coronary Angioplastic, the separate contributions of coronary and collateral blood flow to maximum myocordial perfusion can be obtained.

$FFR_{myo}$ has unique features:
Independent of changes in blood pressure, heart rate and contractility.
Clear breakpoint of 0.75 between significant and non-significant stenoses.
No control artery is needed: applicable in multivessel disease.
Easily and rapidly obtained by intracoronary pressure measurements at maximum vasodilation.

There are monitor systems available for the determination of $FFR_{myo}$ (e.g. WaveMap, Cardiometrics Inc. USA), but they do not have a graphical interface, only numerical displays showing measured values.

SUMMARY OF THE INVENTION

Thus, an object of the invention is to provide improved systems for monitoring physiological variables, in particular for pressure measurements in the coronary vessels, and especially for the reliable determination of Fractional Flow Reserve, $FFR_{myo}$.

Another object is to provide methods for calculation of average pressure values and detection of heart beat using pressure signals from the measurements.

The present invention monitors, determines by measuring and calculation physiological variables related to blood pressure, wherein at least two physiological variables, arterial pressure $P_a$ and distal coronary pressure $P_d$, is detected by and derived from a guidewire-mounted pressure sensor. Myocordial Fractional Flow Reserve ($FFR_{myo}$) is determined by calculating a ratio $P_d/P_a$ from said measured physiological variables ($P_a$, $P_d$) and a graph is formed and displayed of the data resulting from said calculation. The invention also provides an Interactive graphical User Interface system for controlling the performance of and for displaying, in at least one screen on a display in a monitoring unit, intermediate and final results of said invented method.

One advantages of the present invention are that the $FFR_{myo}$-value has a clear breakpoint of 0.75 between significant and non-significant stenoses. This value is easily and rapidly obtained by intracoronary pressure measurements at maximum vasodilation by use of the invented method and system.

Another advantage is that the Interactive graphical User Interface system provides a user-friendly handling.

DETAILED DESCRIPTION OF THE DRAWINGS OF THE INVENTION

The invention relates to a method, a system and an arrangement for monitoring, determining by measurement and calculation and graphically displaying physiological variables related to blood pressure.

Figure 1:
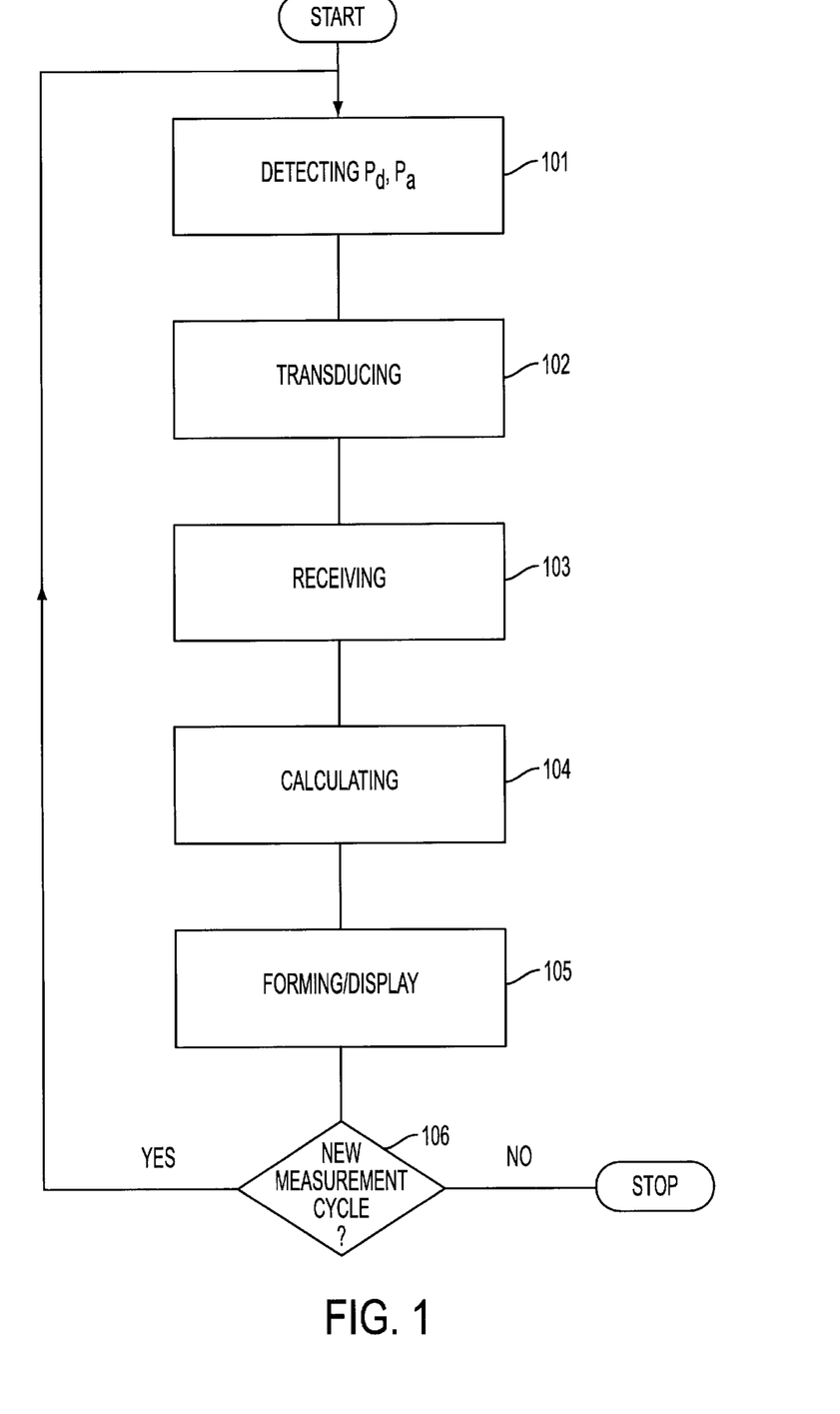
FIG. 1 is a flowchart diagram that discloses a method for monitoring, determining by measurement and calculation and graphically displaying physiological variables related to blood pressure.

Said method is illustrated in flowchart in FIG. 1. The method comprises at least following steps:

step 101:—detecting continuously at least two physiological variables, arterial pressure $P_a$ and distal coronary pressure $P_d$, derived from a guidewire-mounted pressure sensor;

step 102:—transducing said physiological variables to processable signals and delivering said processable signals to a unit being able to process to said processable signals;

step 103:—receiving said processable signals;

step 104:—calculating a ratio $P_d/P_a$ from said measured physiological variables $P_a$, $P_d$ by processing said signals;

step 105:—forming a graph and displaying said graph of the data resulting from said calculation.

step 106:—testing if a new measurement cycle shall be run: if "Yes", than go to step 101, if "No" go to "STOP".

Figure 2:
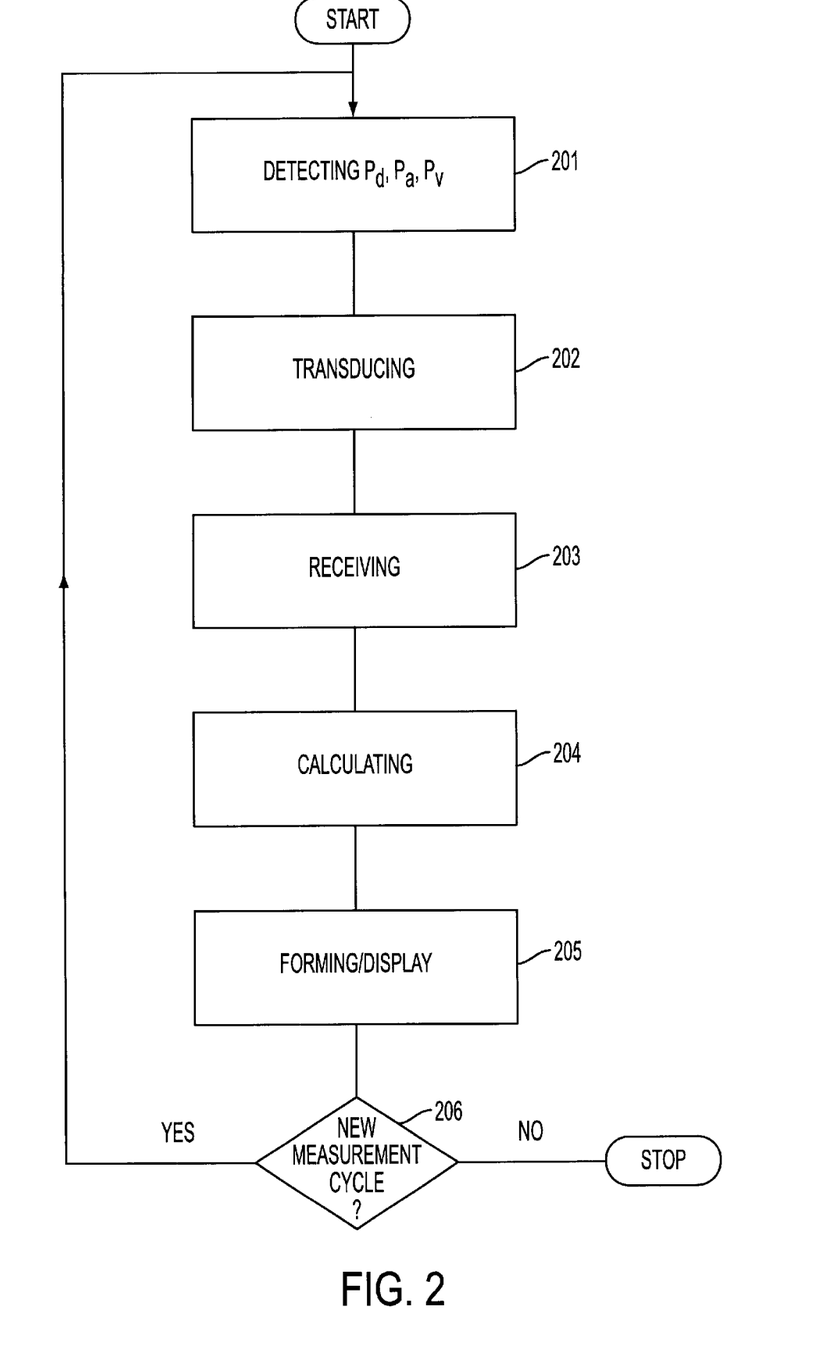
FIG. 2 is a flowchart diagram that discloses a second, modified method for monitoring, determining by measurement and calculation and graphically displaying physiological variables related to blood pressure.

A second, modified method according to the invention is presented in a flowchart, FIG. 2. This modified comprises following steps:

step 201: Besides detecting continuously the two physiological variables, arterial pressure $P_a$ and distal coronary pressure $P_d$, the physiological variable venous pressure $P_v$ is also detected continuously, derived from a guidewire-mounted pressure sensor in the vein;

step 202:—transducing said physiological variables to a processable signals and delivering said processable signals to a unit being able to process said processable signals;

step 203:—receiving said processable signal;

step 204:—calculating a ratio $(P_d-P_v)/(P_a-P_v)$ from the measured physiological variables $P_a, P_d, P_v$ by processing said signals;

step 205:—forming a graph and displaying said graph of the data resulting from said calculation.

step 206:—testing if a new measurement cycle shall be run: if "Yes", than go to step 201, if "No" go to "STOP".

Both described methods may comprise a step of recording and storing either one of the ratio graphs $P_d/P_a$ or $(P_d-P_v)/(P_a-P_v)$ or both said ratio graphs.

Further, both the first and the second methods may include following steps:

marking automatically, or manually by an operator/user, at least one interesting point or portion on the graph;.

using such an interesting point on the graph for calculating a new physiological variable;

In the $FFR_{myo}$ case, said interesting point is a minimum value of the displayed graph.

Figure 3:
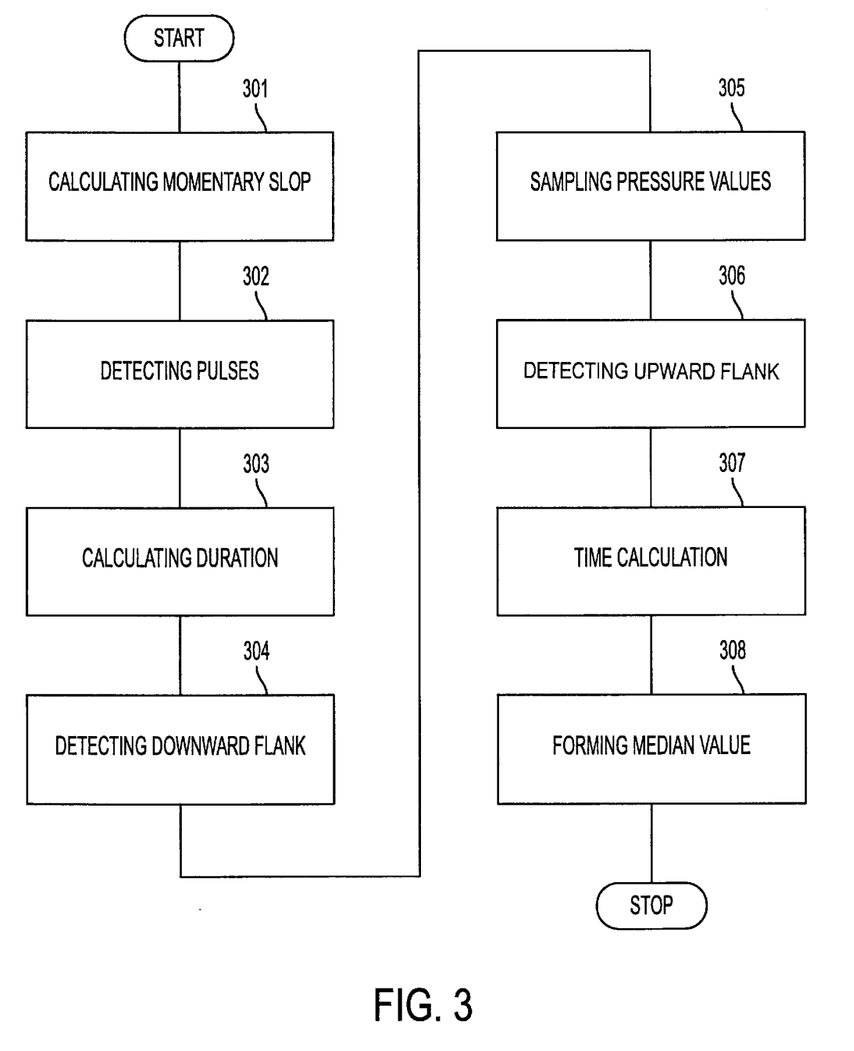
FIG. 3 is a flowchart diagram illustrating a method of heart beat detection in a processable signal representing a pressure signal measured in a coronary vessel in accordance with the invention.

Further, FIG. 3 is a flowchart diagram illustrating a method of heart beat detection in a processable signal representing a pressure signal measured in a coronary vessel in accordance with the invention. This method comprises at least following steps:

step 301:—calculating the momentary slope of the pressure signal continuously;

step 302:—detecting pulses in said processable signal by detecting the characteristic upwards flank of each heart beat by comparing said momentary slope with an adaptively calculated threshold value for said momentary slope; and step 303:—calculating the difference between two consecutive upwards flanks as the duration of a heart beat;

step 304:—detecting a downwards flank of a predetermined magnitude before starting to search for and to detect a consecutive upwards flank;

step 305:—sampling pressure values at a predetermined rate, and comparing each new sampled pressure value with an earlier value for the calculation of said slope;

step 306:—detecting said upwards flank by defining a threshold value that must be exceeded;

step 307:—calculating the time between two heart beats by calculating the time between two upwards flanks of consecutive heart beats;

step 308:—calculating the adaptive threshold value by continuously storing a number of calculated slopes above and below a certain minimum value, and forming a median value thereof.

Figure 4:
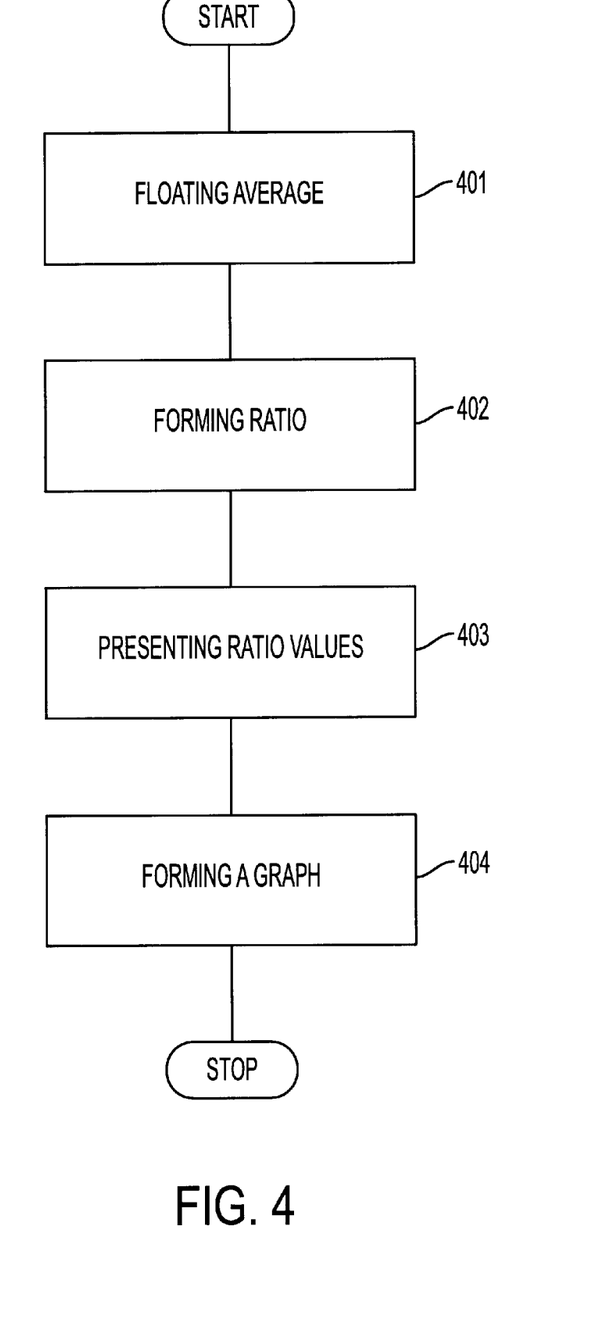
FIG. 4 is a flowchart diagram illustrating a method for the calculation of $FFR_{myo}$ according to the invention.

FIG. 4 is a flowchart diagram illustrating a method for the calculation of $FFR_{myo}$ according to the invention. The method comprises at least following steps:

step 401:—forming a floating average of a measured heart pressure over a number of heart beats, wherein the calculation is based on the continuous detection of heart beats; and step 402:—forming continuously a ratio between two calculated average pressures, each pressure value being an integral under the curve representing the pressure;

step 403:—presenting the ratio values as discrete points; and step 404:—forming a graph.

Embodiments for implementing the disclosed invented method will now be described.

Figure 5:
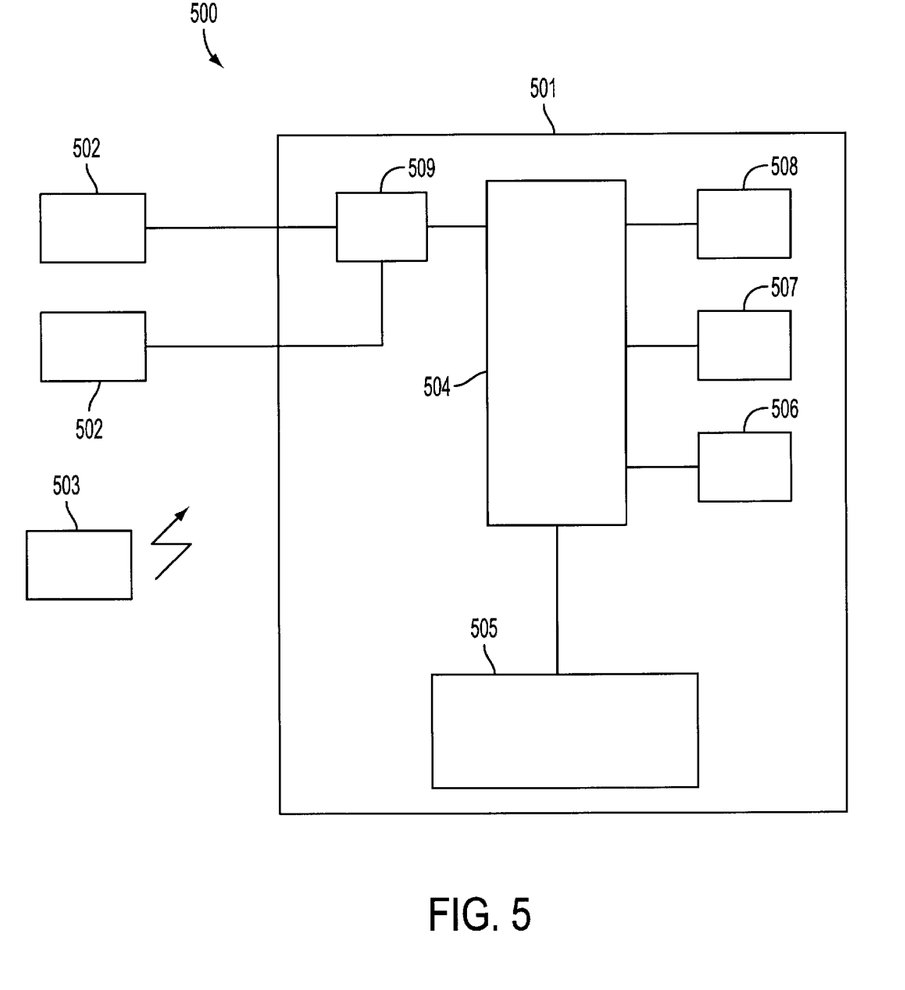
FIG. 5 discloses a block diagram of a preferred embodiment of a measurement system according to the invention.

FIG. 5 discloses a block diagram of a preferred embodiment of a measurement system 500 according to the invention. Said system comprises a monitoring unit 501, connected to at least two sensor elements 502, each sensor element 502 being capable of detecting continuously at least two physiological variables, arterial pressure $P_a$ and distal coronary pressure $P_d$. The monitoring unit 501 comprises a control unit 503, operable via a remote control 504, and a display element 505 for showing recorded graphs of the measurements. Said display can be a cathode-ray tube screen or a flat screen. A computer program storage 506, a storage 507 for storing recorded signals, calculated values, graphs etc. and a storage 508 for storing a menu system are connected to the control unit. Even though said storages are illustrated as different blocks in the figure, they may be included in the same storage device. An element able to receiving a delivered or transmitted processable signal generated in the element being capable of continuously detecting at least two physiological variables, arterial pressure $P_a$ and distal coronary pressure $P_d$.

The sensor elements 502 being capable of detecting continuously at least two physiological variables, arterial pressure $P_a$ and distal coronary pressure $P_d$ can have separate transducing elements or be designed to deliver a processable signal, without a transducer element. Many standard sensor elements is capable of transducing said physiological variables to processable signals, such as digital or analogue signals and delivering said processable signals to a unit being able to process said processable signals. However, a separate transducing element being capable of transducing said physiological variables to processable signals and deliver or transmit the signals may have to be added to some sensor instruments. The unit, being able to process said processable signals, is in this embodiment the monitoring unit 501. The guide wire/catheter assembly can comprise any standard catheter for measurement of blood pressure, where the actual pressure sensor is located externally of the body during measurement, the pressure being conveyed by the liquid column inside the catheter.

The guide wire, a guidewire-mounted pressure sensor, may be the PressureWire$^R$ available from RADI Medical, Sweden. Various aspects and features of said device are protected by patents ( ), and there are several pending applications.

For illustration the use of the measurement system will now be described, and with reference to the use of said a guidewire-mounted pressure sensor as a sensor element.

Said monitoring unit can comprise a receiving element 509 between the sensor element and the control unit, said receiving element 509 being capable of receiving said processable signals. Said element 509 can be implemented as a receiver and/or an adaptation circuit, such as a filter circuit. However, such a element may not be necessary in some applications of the invention.

Element being capable of calculating a ratio $P_d/P_a$ from said measured physiological variables $P_a, P_d$ by processing said signals is a computer program or computer software, stored in one of the storages connected to the control unit and used by said unit during the measurement cycles. The control unit is implemented as a micro-computer or a CPU (Computer Processing Unit) or similar and comprises also necessary in-/out circuits.

Element being capable of forming a graph and displaying said graph of the data resulting from said calculation is also a computer program or computer software, stored in one of the storages connected to the control unit and used by said unit during the measurement cycles. Said element may be regarded as a part of interactive graphical user interface for selection of functions from a menu system stored in one of the computer storages connected to the control unit. The display shows different screens and menus from which the desired functions are selectable via the remote control. The interactive graphical user interface system comprises function-activating buttons displayed in different screens and said buttons are operated by an user/operator via the remote control and each button activates a predetermined function of said system.

In another embodiment of the invented system, it is of interest to determine $FFR_{myo}$ as the ratio $$FFR_{myo} = (P_d - P_v)/(P_a - P_v).$$

For this purpose, the system has to be provided with an element being capable of detecting continuously the physiological variable venous pressure, $P_v$, and element being capable of transducing said physiological variable to a processable signal and delivering said processable signal to an unit, like a monitoring unit, being able to process said processable signals. The element being capable of detecting continuously $P_v$ can be a guide wire/catheter assembly having transducers, such as pressure sensors attached thereto. Many standard sensor elements is capable of transducing said physiological variable to processable signal, such as digital or analogue signal and delivering said processable signal to a unit being able to process said processable signals and transmit said signal to the next circuit. However, separate element being capable of transducing said physiological variables to processable signals and deliver or transmit the signals can have to be added to some sensor instruments. The unit being able to process said processable signals is in this embodiment the monitoring unit. The guide wire/catheter assembly can comprise any standard catheter for measurement of blood pressure, where the actual pressure sensor is located externally of the body during measurement, the pressure being conveyed by the liquid column inside the catheter. The system is also provided with an element being capable of receiving said processable signal, an element being capable of calculating a ratio $(P_d-P_v)/(P_a-P_v)$ from the measured physiological variables $P_a$, $P_d$, $P_v$ by processing said signals and element being capable of forming a graph and displaying said graph of the data resulting from said calculation. Said systems are similar to the corresponding element described in the first preferred embodiment of the system.

The system is also provided with memory function for storing recordings, so as to be able to refer back to old measurements. Said memory function involves element being capable of recording and storing either one of the ratio graphs $P_d/P_a$ or $(P_d-P_v)/(P_a-P_v)$ or both said ratio graphs. Said element is implemented as software in the control unit and the storages.

Element being capable of marking automatically, or manually by an operator/user, at least one interesting point or portion on the graph, said element being comprised in the interactive graphical interface system, and element being capable of using such an interesting point on the graph for calculating a new physiological variable are also implemented as software used by the control unit. When determining the FFR-value, said interesting point is the minimum value of the displayed pressure ratio-graph.

The invented measurement system may comprise an arrangement for heart beat detection in a processable signal representing a pressure signal measured in a coronary vessel. Said arrangement comprises:

element being capable of calculating the momentary slope of the pressure signal continuously;

element being capable of detecting pulses in said processable signal by detecting the characteristic upwards flank of each heart beat by comparing said momentary slope with an adaptively calculated threshold value for said momentary slope; and element being able of calculating the difference between two consecutive upwards flanks as the duration of a heart beat; further, element being capable of detecting a downwards flank of a predetermined magnitude before starting to search for and to detect a consecutive upwards flank;

comprising element being capable of sampling pressure values at a predetermined rate, and comparing each new sampled pressure value with an earlier value for the calculation of said slope; and element being capable of detecting said upwards flank by defining a threshold value that must be exceeded;

element being capable of calculating the time between two heart beats by calculating the time between two upwards flanks of consecutive heart beats; and element being capable of calculating the adaptive threshold value by continuously storing a number of calculated slopes above and below a certain minimum value, and forming a median value thereof. Said median value can be weighted by a percentage, preferably 80%.

The arrangement for heart beat detection in a processable signal representing a pressure signal measured in a coronary vessel and its different elements, listed above, is implemented as a computer program or computer software, stored in one of the storages connected to the control unit and used by said control unit during the measurement cycles.

The invented system also comprises an arrangement for the calculation of $FFR_{myo}$ values. Said arrangement comprises element being capable of forming a floating average of a measured heart pressure over a number of heart beats, wherein the calculation is based on the continuous detection of heart beats, and element being capable of continuously forming a ratio between two calculated average pressures, each pressure value being an integral under the curve representing the pressure, the $FFR_{myo}$ being presented as a discrete point, and element being capable of forming a graph. Even this arrangement for calculating FFR-values is implemented as a computer program or computer software, stored in one storage connected to the control unit and used by said control unit during the measurement cycles.

The practical use of the invented method and system will be now be described.

The signals from the two pressure sensors must be calibrated prior to measurement. This is done by immersing the sensor in saline, ascertaining that no liquid column is present above the actual sensor element. By activating a Cal button on the display, the calibration is done.

The catheter is calibrated against air by simply opening the catheter to the ambient atmosphere, and activating a corresponding Cal button, which is displayed on a selected menu of the system.

The catheter is inserted to the desired location proximally of a suspected stenosis. The sensor is brought to the catheter opening. Because of factors such as local environment inside the vessel, imperfections in the manufacturing, it is more likely than not that the two sensors will not show the same pressure value. In order to compensate for this the readings are "equalized" by pressing a EQUAILIZE button on the remote control. This equailizing is a software implemented adjustment of the off-set, i.e. the difference between the two is eliminated by adding or subtracting a suitable value from one of the readings.

Then the sensor is brought past the stenosis. Adenosine is injected into the catheter and further into the blood flow. This will cause a simulation of labor, i.e. the heart will act as if the patient performed a physical effort. The half life of the adenosine, i.e. the time after which the labor effect has been reduced to 50% is at the most 5–10 heart cycles. Thus, the time during which the effect of the adenosine is constant, and during which time the measurements preferably should be made is shorter.

Pressure values are sampled, at present at a rate of 100 Hz, although this is not critical.

The RECORD function is activated before the injection of adenosine, thus initiating the sampling, and is turned off when the physician assesses that the effect has become so low that no more measurements are meaningful.

The monitor displays the $P_d/P_a$ continuously as a graph, and when the recording has been terminated, the system automatically marks the point on the curve representing the minimum, which then should represent $FFR_{myo}$, by placing a vertical line across the screen at that point (of course any other kind of marker can be used). This enables the physician to directly assess whether the calculated value is reasonable. If the minimum is due to an artifact, e.g. a negative "spike" in the curve, it can immediately be detected by inspection. The marker (vertical line) can be moved to a more proper point, and the system will immediately display the FFR-value corresponding to the point selected.

The marker function can also be activated during recording to mark certain events during measurement. For example, the physician can mark the point where the patient coughs, or when the sensor is moved to another location etc.

This is especially useful for multiple stenoses, where the operator can mark a plurality of measurement points before and after each stenosis, and the system can be activated to use said points for the calculation of several FFR-values.

The method for detection of pulse beats in a pressure signal according to the invention utilizes the characteristic upwards flank in the beginning of each heart beat. The pressure rises rapidly in a way that does not take place anywhere else during the normal heart cycle. By comparing each new value with a value that was stored a certain time previously, the momentary slope (derivative) of the pressure signal is calculated continuously. The time between the two values can be selected such that slopes less than the upward flanks of the heart beat are suppressed. The beginning of the heart beat is defined as the point where the slope exceed a certain threshold value. The time between two heart beats, i.e. the cycle time, is then defined as the time between two upwards flanks. The threshold value is calculated adaptively as a weighted average or median value of a certain number of slopes previously recorded. The number of stored slopes will determine how rapidly the system is "tuned in" on changed amplitudes. The systole can be calculated as the highest point between two upwards flanks, the diastole as the lowest.

The system continuously calculates the difference in pressure between two samples, at a certain distance (in time). The difference will be a measure of the slope (derivative) in the curve. The pressure wave has a distinct upwards flank that distinguishes from other parts of the pressure. With an adaptive threshold value the pressure wave can be detected at each upwards flank. The time between each flank then becomes the time between two pulse beats. When the system finds an upwards flank above the threshold value it resets and searches for a downwards flank, the "backside" of the pulse wave. The system does not detect a new upwards flank until it finds a downwards flank of sufficient magnitude, in order to avoid "double detections".

The adaptivity of the threshold values is achieved by continuously store a certain number of calculated slopes above and below a certain minimum value (e.g. +/−3 mmHg). Then the threshold values can be calculated as the median of these, weighted by a percentage. 80% of the median has proven good. The system is then able to detect pulses with strongly varying amplitude, despite variation in base line and frequency.

In order to reduce the risk of erroneous detection there is a limit for the smallest allowed distance between two upwards flanks (maximum heart rate). Occasional disturbances in the form of fast spikes or the like can be avoided by adding an upper limit for the slope. A further technique to reduce the risk of erroneous detection is if the upwards flank is not "approved" until a downwards flank has been detected, within a reasonable time.

An Interactive graphical User Interface system for controlling the performance of a method according to any of claims 1–12 and for displaying, in at least one screen on a display of a monitoring unit, intermediate and final results of said method claims 1–12.

A computer program product directly loadable into the internal memory storage of a processing means within the control unit, comprising the software code means for performing the steps of any claims 1–12.

The computer program product can be stored on a computer usable medium, comprising readable program for causing a processing means in a control unit to control an execution of the steps of any of the claims 1–12.

The method is implemented by means of a computer program product comprising the software code means for performing the steps of the method. The computer program product is run on the processing means of the control unit in the monitoring unit. The computer program is loaded directly or from a computer usable medium, such as a floppy disc, a CD, the Internet etc.

The present invention is not limited to the above-described preferred embodiments. Various alternatives, modifications and equivalents may be used. Therefore, the above embodiments should not be taken as limiting the scope of the invention, which is defined by the appended claims.

What is claimed is:

1. Method for monitoring, determining by measurement and calculation and graphically displaying physiological variables related to blood pressure, comprising at least the following steps:

detecting continuously at least two physiological variables, arterial pressure ($P_a$) and distal coronary pressure ($P_d$), derived from a guidewire-mounted pressure sensor;

transducing said physiological variables to processable signals and delivering said processable signals to a unit being able to process said processable signals;

receiving said processable signals;

forming a floating average of a measured heart pressure over a number of heart beats;

calculating a ratio $P_d/P_a$ from said measured physiological variables ($P_a$, $P_d$) by processing said signals, wherein the calculation is based on the continuous detection of heart beats and continuously forming a ratio between two calculated average pressures;

forming a graph and displaying said graph of the data resulting from said calculation.

2. Method according to claim 1, characterized by the following steps:
   detecting continuously the physiological variable venous pressure ($P_v$);
   transducing said physiological variable to a processable signal and delivering said processable signal the unit being able to process to said processable signals;
   receiving said processable signal;
   calculating a ratio $(P_d-P_v)/(P_a-P_v)$ from the measured physiological variables ($P_a$, $P_d$, $P_v$) by processing said signals;
   forming a graph and displaying said graph of the data resulting from said calculation.

3. Method according to claim 1, characterized by the following step:
   recording and storing either one of the ratio graphs $P_d/P_a$ or $(P_d-P_v)/(P_a-P_v)$ or both said ratio graphs.

4. The method according to claim 1, wherein each average pressure value used in the calculation is an integral under a curve representing the measured heart pressure, and the ratio values are presented as discrete points on the graph.

5. Interactive graphical user interface system for controlling the calculation of and for displaying, in at least one screen on a display in a monitoring unit, intermediate and final results of the method of claim 1.

6. A computer program product directly loadable into an internal memory storage of a processor within a control unit, comprising software code for performing the steps of claim 1.

7. A computer program product capable of being stored on a computer usable medium, comprising a computer readable program for causing a processor in a control unit to control an execution of the steps of claim 1.

8. A method of heart beat detection in a processable signal representing a pressure signal measured in a coronary vessel, comprising at least the following steps:
   detecting continuously at least two physiological variables, arterial pressure ($P_a$) and distal coronary pressure ($P_d$), derived from a guidewire-mounted pressure sensor;
   transducing said physiological variables to processable signals and delivering said processable signals to a unit being able to process said processable signals;
   receiving said processable signals;
   calculating a ratio $P_d/P_a$ from said measured physiological variables ($P_a$, $P_d$) by processing said signals;
   forming a graph and displaying said graph of the data resulting from said calculation;
   calculating a momentary slope of the pressure signal continuously;
   detecting pulses in said processable signal by detecting a characteristic upwards flank of each heart beat by comparing said momentary slope with an adaptively calculated threshold value for said momentary slope; and calculating a difference between two consecutive upwards flanks as the duration of a heart beat.

9. The method according to claim 8, comprising detecting said upwards flank by defining a threshold value that must be exceeded.

10. The method according to claim 8, comprising calculating the time between two heart beats by calculating the time between two upwards flanks of consecutive heart beats.

11. The method according to claim 8, wherein the calculation of the adaptive threshold value comprises continuously storing a number of calculated slopes above and below a certain minimum value and forming a median value thereof.

12. The method according to claim 8, further comprising detecting a downwards flank of a predetermined magnitude before starting to search for and to detect a consecutive upwards flank.

13. The method according to claim 8, comprising sampling pressure values at a predetermined rate, and comparing each new sampled pressure value with an earlier value for the calculation of said slope.

14. Method for monitoring, determining by measurement and calculation and graphically displaying physiological variables related to blood pressure, comprising at least the following steps:
   detecting continuously at least two physiological variables, arterial pressure ($P_a$) and distal coronary pressure ($P_d$), derived from a guidewire-mounted pressure sensor;
   transducing said physiological variables to processable signals and delivering said processable signals to a unit being able to process said processable signals;
   receiving said processable signals;
   calculating a ratio $P_d/P_a$ from said measured physiological variables ($P_a$, $P_d$) by processing said signals;
   forming a graph and displaying said graph of the data resulting from said calculation;
   marking automatically, or manually by an operator/user, at least one interesting point or portion on the graph; and
   using such an interesting point on the graph for calculating a new physiological variable.

15. Method according to claim 14, wherein said interesting point is a minimum value of the displayed graph.

16. System for monitoring, determining by measurement and calculation and graphically displaying physiological variables related to blood pressure, comprising:
   a graphical user interface for selection of functions from a menu system;
   a sensor element, said sensor element being capable of detecting continuously at least two physiological variables, arterial pressure ($P_a$) and distal coronary pressure ($P_d$) and delivering processable signals to a unit being able to process to said processable signals;
   a ratio element, said ratio element being capable of calculating a ratio $P_d/P_a$ from said measured physiological variables ($P_a$, $P_d$) by processing said processable signals;
   a display element, said display element being capable of forming a graph and displaying said graph of the data resulting from said calculation;
   a marking element, said marking element being capable of marking automatically, or manually by an operator/user, at least one interesting point or portion on the graph; and
   a calculating element, said calculating element being capable of using said interesting point on the graph for calculating a new physiological variable.

17. System according to claim 16, wherein said interesting point is a minimum value of the displayed graph.

18. A system for heart beat detection, comprising:
   a graphical user interface for selection of functions from a menu system;
   a sensor element, said sensor element being capable of detecting continuously at least two physiological variables, arterial pressure ($P_a$) and distal coronary pressure ($P_d$) and delivering processable signals to a unit being able to process to said processable signals;

a ratio element, said ratio element being capable of calculating a ratio $P_d/P_a$ from said measured physiological variables ($P_a$, $P_d$) by processing said processable signals;

a display element, said display element being capable of forming a graph and displaying said graph of the data resulting from said calculation;

a slope element, said slope element being capable of calculating a momentary slope of the processable signals continuously;

a pulse detecting element, said pulse detecting element being capable of detecting pulses in said processable signals by detecting a characteristic upwards flank of each heart beat by comparing said momentary slope with an adaptively calculated threshold value for said momentary slope; and a duration element, said duration element being capable of calculating a difference between two consecutive upwards flanks as a duration of a heart beat.

19. A system according to claim 18, further comprising a downwards flank element, said downwards flank element being capable of detecting a downwards flank of a predetermined magnitude before starting to search for and to detect a consecutive upwards flank.

20. A system according to claim 18, further comprising a sampling element, said sampling element being capable of sampling pressure values at a predetermined rate, and comparing each new sampled pressure value with an earlier value for the calculation of said momentary slope.

21. A system according to claim 18, further comprising an upwards flank element, said upwards flank element being capable of detecting said upwards flank by defining a threshold value that must be exceeded.

22. A system according to claim 18, further comprising a beat element, said beat element being capable of calculating a time between two heart beats by calculating a time between two upwards flanks of consecutive heart beats.

23. A system according to claim 18, further comprising a threshold value element, said threshold value element being capable of calculating an adaptive threshold value by continuously storing a number of calculated slopes above and below a certain minimum value, and forming a median value thereof.

24. System for monitoring, determining by measurement and calculation and graphically displaying physiological variables related to blood pressure, comprising:

a graphical user interface for selection of functions from a menu system;

a sensor element, said sensor element being capable of detecting continuously at least two physiological variables, arterial pressure ($P_a$) and distal coronary pressure ($P_d$) and delivering processable signals to a unit being able to process to said processable signals;

a floating average element, said floating average element being capable of calculating a floating average of a measured heart pressure over a number of heart beats by processing said processable signals, wherein the calculation is based on the continuous detection of heart beats;

a ratio element, said ratio element being capable of continuously calculating a ratio between two calculated average pressures $P_d/P_a$ from said floating average of measured physiological variables ($P_a$, $P_d$); and a display element, said display element being capable of forming a graph and displaying said graph of the data resulting from said calculation.

25. A system according to claim 24, wherein said graphical user interface comprises function-activating buttons to be operated by a user/operator and for activating predetermined functions of said system.

26. System according to claim 24, wherein:

the sensor element is capable of detecting continuously the physiological variable venous pressure ($P_v$) and delivering a corresponding processable signal to the floating average element;

the ratio element is capable of calculating a ratio ($P_d-P_v$)/($P_a-P_v$) from a floating average of the measured physiological variables ($P_a$, $P_d$, $P_v$) calculated by the floating average element; and the display element is capable of forming a graph and displaying said graph of the data resulting from said calculation.

27. System according to claim 26, further comprising:

a memory element, said memory element being capable of recording and storing either one of ratio graphs $P_d/P_a$ or ($P_d-P_v$)/($P_a-P_v$) or both said ratio graphs.

28. A system according to claim 24, wherein each pressure value used in the calculation comprises an integral under a curve representing the pressure, and ratio values are presented as discrete points.

29. A system for monitoring, determining by measurement and calculation and graphically displaying physiological variables related to blood pressure, comprising:

a graphical user interface for selection of functions from a menu system;

a sensor element, said sensor element being capable of detecting continuously at least two physiological variables, arterial pressure ($P_a$) and distal coronary pressure ($P_d$) delivering a processable signals to a unit being able to process to said processable signals;

a floating average element, said floating average element being capable of calculating a floating average of a measured heart pressure over a number of heart beats by processing said processable signals, wherein the calculation is based on the continuous detection of heart beats;

a ratio element, said ratio element being capable of calculating a ratio $P_d/P_a$ from said measured physiological variables ($P_a$, $P_d$) by processing said processable signals; and a display element, said display element being capable of forming a graph and displaying said graph of the data resulting from said calculation.

* * * * *